United States Patent [19]

Morioka et al.

[11] Patent Number: 5,093,243
[45] Date of Patent: Mar. 3, 1992

[54] PROCESS FOR THE SEPARATION AND RECOVERY OF NOSIHEPTIDE

[75] Inventors: Satoshi Morioka; Makoto Shida, both of Yokohama, Japan

[73] Assignee: Rhone Poulenc Sante, Courbevoie, France

[21] Appl. No.: 874,485

[22] Filed: Jun. 16, 1986

[30] Foreign Application Priority Data

Jun. 19, 1985 [JP] Japan .................................. 60-133552

[51] Int. Cl.$^5$ ........................ C12P 21/04; C12P 17/18
[52] U.S. Cl. .................................... 435/71.3; 435/119
[58] Field of Search ...................... 435/119, 71.3, 886, 435/128, 130

[56] References Cited

U.S. PATENT DOCUMENTS 3,155,581 11/1964 Pinnert et al. ...................... 435/128
4,384,043 5/1983 Martin et al. .......................... 435/71
4,584,134 4/1986 Morioka et al. ..................... 540/460

*Primary Examiner*—Douglas W. Robinson
*Assistant Examiner*—Irene Marx
*Attorney, Agent, or Firm*—Morgan & Finnegan

[57] ABSTRACT

Nosiheptide is recovered from a cultivation mixture obtained by cultivating a Nosiheptide-producing strain of Streptomyces by adding a water-miscible organic solvent, removing mycelia, precipitating Nosiheptide by adding water, which may be acidified, and recovering the Nosiheptide.

8 Claims, No Drawings

PROCESS FOR THE SEPARATION AND RECOVERY OF NOSIHEPTIDE

The present invention relates to the separation and recovery of the antibiotic Nosiheptide from a cultivation mixture containing it.

Nosiheptide (also called 9671RP) is an antibiotic produced by a strain of the genus Streptomyces. It is used as a feed additive for animals.

Nosiheptide is prepared by cultivation of a Nosiheptide-producing strain of the genus Streptomyces (Japanese Patent Publication No. 880/1965 or U.S. Pat. No. 3155581). It is known to separate and recover Nosiheptide from a cultivation mixture using a cyclic ether as an extractant (see Japanese Patent Application No. 121273/1983 or European Specification 133 079) or by adding an inorganic salt after a solvent treatment. However, these methods are not satisfactory.

Generally, the separation and recovery of an antibiotic from a cultivation mixture is carried out by mixing the cultivation mixture with a solvent, separating the mycelia insoluble in the solvent, distilling off the solvent by heating or in vacuo, and recovering the precipitated particles of antibiotic by filtering or centrifuging. This process cannot be easily operated with Nosiheptide, as the purity of Nosiheptide deteriorates, since a particle of Nosiheptide is very small.

The present invention provides a method for separation and recovery of Nosiheptide in high purity and high yield from a cultivation mixture, by improving the sedimentation and filtering characteristics of the Nosiheptide particles.

The process of the present invention for the separation and recovery of Nosiheptide from a cultivation mixture obtained by cultivating a Nosiheptide-producing strain of the genus Streptomyces, comprises adding an organic solvent for Nosiheptide, which is miscible with water in all proportions to said mixture, separating a solvent-insoluble portion having mycelia as a main component, adding water or water containing acid to the solution containing Nosiheptide to precipitate Nosiheptide, and recovering the Nosiheptide so precipitated.

*Streptomyces actuosus* (NRRL 2954; ATCC 25421) of the genus Streptomyces and its mutants are known Nosiheptide-producing strains. The cultivation mixture containing Nosiheptide is obtained by cultivating such a strain by the method described in Japanese Patent Publication No. 880/1965 or U.S. Pat. No. 3155581. The cultivation mixture contains carbohydrates, inorganic salts and other components of the fermentation medium, mycelia, Nosiheptide and the like. Nosiheptide accumulates on the surface of the mycelia which are mainly composed of actinomycetes having a complicated surface structure.

In the process of this invention the cultivation mixture (broth) is mixed with a solvent, e.g. a ketone, alcohol, furan or the like, which is miscible with water, preferably acetone, methyl ethyl ketone, an aliphatic alcohol having less than 4 carbon atoms, or tetrahydrofuran.

The cultivation mixture may be subjected to the solvent treatment, either as broth following a dehydration treatment with a mechanical device, such as a centrifugal separator or filter, or as crude broth without any dehydration treatment. However, it is economically advantageous to use crude broth.

The amount of the solvent used depends on the kind of solvent, and the amount of water and Nosiheptide in the cultivation mixture. For example, when tetrahydrofuran, acetone or ethanol is used, the amount is generally from 0.5 to 5 volumes, preferably 1.5 to 2.5 volumes, per volume of the cultivation mixture.

The solvent treatment is generally performed in a stirring tank with an outlet for insoluble matter at the bottom. The time for the treatment is usually 0.5 to 3 hours, preferably 1 to 2 hours, and the temperature is usually 5° to 80° C., preferably room temperature (about 20° C.) to 60° C.

The pH of the cultivation mixture used in the treatment varies according to the cultivation conditions. It is preferable to adjust pH to within the range of 3 to 10, more preferably 5 to 9, for the treatment.

After the solvent treatment, the insoluble portion having mycelia as a main component is separated from the mixture of cultivation mixture and solvent to obtain a solution of Nosiheptide.

Water or water containing acid is then added to the solution of Nosiheptide obtained to separate the Nosiheptide. The amount of water, or water containing acid, to be added is 0.3 to 2.0 volumes, preferably 0.4 to 1.0 volume, per volume of the solution containing Nosiheptide. Separation is not good when a small amount of water is added; but if too much water is added, the filter characteristics worsen.

As the acid, an inorganic acid such as sulphuric acid, hydrochloric acid, or nitric acid, or an organic acid such as acetic acid, can be used by itself or in mixture, in such an amount that the pH value of the solution is 3 to 7, preferably 5 to 6, when water containing acid is added to the solution. When the pH is too high, the precipitation rate of the Nosiheptide and its chemical stability worsen.

The addition of water, or water containing acid, should be done gradually with stirring and good mixing. Generally it takes 0.1 to 5 hours, preferably 0.5 to 3 hours, to add the water or water containing acid.

The manner of adding water or water containing acid greatly influences the particle size of the Nosiheptide and its purity. For example, when adding 4m³ of water to 6 m³ of the solution containing Nosiheptide in a 10m³ mixing vessel, adding fast (10 to 30 minutes, 0.4 to 0.13 m³/minute) generates particles of less than 0.14 μm and 85 to 90% of purity, while adding gradually and continuously (0.5 to 5 hours, 0.13 to 0.013 m³/minute), generates particles of 1 to 2 μm and 95 to 98% of purity.

The Nosiheptide normally separates in crystalline form. Recovery of the separated Nosiheptide from the solution is easily performed using a centrifugal separator or filter.

In the process of this invention, adding water or water containing acid over 0.1 to 5 hours, preferably 0.5 to 3 hours, improves sedimentation and filter characteristics of the Nosiheptide particles, which leads to easy operation.

The Nosiheptide recovered sometimes contains a small amount of metal. If it is necessary to remove such metal, the Nosiheptide should be dissolved in an appropriate solvent and treated with activated charcoal, silica gel or an ion exchange resin.

The present invention is illustrated by the following Examples.

EXAMPLE 1

A mixing tank with an outlet at the bottom is charged with 100 parts by volume of cultivation mixture (broth) obtained by cultivating *Streptomyces actuosus*. 200 parts by volume of tetrahydrofuran are added and the mixture is stirred at 60° C. for 1 hour. The mycelia are then separated from the extract by centrifugal separation. 260 parts by volume of extract are obtained.

The composition of the cultivation mixture is as follows:
mycelia: 7.5 wt %
carbohydrates: 2.0
inorganic salts: 0.5
Nosiheptide: 0.5
water: 89.5
pH: 5.6

Liquid chromatography shows that the extract solution contains 0.187 wt % of Nosiheptide (yield 90.0 wt %).

150 parts by volume of water containing 0.2 parts by volume of concentrated sulphuric acid are then added drop by drop with uniform stirring to 200 parts by volume of the above solution in the mixing tank over 1 hour. All the contents are then discharged and filtered to recover Nosiheptide.

By liquid chromatography analysis, the concentration of Nosiheptide in the separated solvent is 0.005 wt %. The purity of the recovered Nosiheptide is 98.0 wt %, and the yield is 95.0 wt %.

EXAMPLE 2

A mixing tank, as in Example 1, is charged with 100 parts by volume of cultivation mixture (broth) and the pH is adjusted to 8.0 by adding 10 wt % of sodium hydroxide. 200 parts by volume of acetone (instead of tetrahydrofuran) are then charged and the treatment is the same as in Example 1. The recovered solution containing Nosiheptide is 240 parts by volume. By liquid chromatography analysis, the Nosiheptide in the solution is 0.193 wt % and the recovery is 85.0 wt %.

140 parts by volume of water containing 0.2 parts by volume of concentrated sulphuric acid are then added in drops with stirring to 200 parts by volume of the above solution in the mixing tank over 1 hour. All the contents are then discharged and filtered to recover Nosiheptide as in Example 1. The concentration of Nosiheptide in the separated solvent is 0.008 wt %. The purity of the recovered Nosiheptide is 98.0 wt %, and the yield is 92.5 wt %.

EXAMPLE 3

300 parts by volume of water are added in drops with stirring over 1 hour to a mixing tank charged with 200 parts by volume of a solution containing Nosiheptide obtained by mixing 100 parts by volume of broth with 200 parts by volume of acetone and removing insoluble matter as in Example 2. The Nosiheptide is then recovered by the method of Example 1. The concentration of Nosiheptide in the separated solvent is 0.007 wt %, the purity of the recovered Nosiheptide is 97.0 wt %, and the yield is 91.0 wt %.

Comparative Example 1

In the process of Example 1, the cultivation mixture and the solvent are mixed and stirred, and the mixture is heated to distill tetrahydrofuran to precipitate Nosiheptide. The particles of Nosiheptide thus separated out, however, cannot be recovered by filtration, since they form an emulsion which cannot be filtered. The particles are separated with a centrifugal separator (5,000 G, 20 minutes) and the precipitate is washed. The purity of Nosiheptide is 70.0 wt % and yield is 80.0 wt %.

We claim:

1. In a process for the separation and recover of Nosiheptide obtained from a Nosiheptide-producing strain of Streptomyces, by cultivating said strain of the genus Streptomyces to produce a nosiheptide-containing cultivation mixture, adding to said cultivation mixture an organic solvent for nosiheptide, said solvent being miscible with water in all proportions, to produce an aqueous organic solution of nosiheptide and a solvent-insoluble portion having mycelia as a main component, separating said solvent-insoluble portion from said aqueous organic solution, and isolating nosiheptide from the separated aqueous organic solution, the improvement which comprises precipitating nosiheptide from the said separated aqueous organic solution by adding water, or water-containing acid, thereto, and recovering said precipitated nosiheptide.

2. Process according to claim 1 in which the said organic solvent is an aliphatic alcohol having less than 4 carbon atoms, acetone, methyl ethyl ketone, or tetrahydrofuran.

3. Process according to claim 2 in which the said organic solvent is added to the cultivation mixture in a proportion of 1.5 to 2.5 volumes per volume of the said mixture.

4. Process according to claim 1 in which the said organic solvent is added to the cultivation mixture in a proportion of 0.5 to 5 volumes per volume of the said mixture.

5. Process according to claim 1 in which the amount of water, or water containing acid, added to the solution containing Nosiheptide is 0.3 to 2.0 volumes per volume of the said solution.

6. Process according to claim 1 in which water containing acid is added to the solution containing Nosiheptide in a proportion of 0.4 to 1.0 volume per volume of the solution, and the amount of acid in said water is sufficient to adjust the pH value of the solution to 5 to 6.

7. Process according to claim 1 in which the water, or water containing acid, is added gradually and continuously over a period of 0.5 to 5 hours.

8. Process according to claim 1 in which the cultivation mixture is obtained by cultivating *Streptomyces actuosus*.

* * * * *